US012642647B2

(12) United States Patent
Jin et al.

(10) Patent No.: US 12,642,647 B2
(45) Date of Patent: Jun. 2, 2026

(54) SPLIT TYPE PRECISELY-ANCHORABLE TRANSCATHETER VALVE-IN-RING SYSTEM

(71) Applicant: BEIJING BALANCE MEDICAL TECHNOLOGY CO., LTD., Beijing (CN)

(72) Inventors: Lei Jin, Beijing (CN); Lai Wei, Beijing (CN); Kangjian Wu, Beijing (CN); Jia Wu, Beijing (CN); Zhihao Fan, Beijing (CN); Liyan Li, Beijing (CN)

(73) Assignee: BEIJING BALANCE MEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 18/710,528

(22) PCT Filed: Nov. 17, 2022

(86) PCT No.: PCT/CN2022/132662
§ 371 (c)(1),
(2) Date: May 15, 2024

(87) PCT Pub. No.: WO2023/088392
PCT Pub. Date: May 25, 2023

(65) Prior Publication Data
US 2025/0107888 A1 Apr. 3, 2025

(30) Foreign Application Priority Data

Nov. 17, 2021 (CN) .......................... 202111361458.6

(51) Int. Cl.
*A61F 2/24* (2006.01)
(52) U.S. Cl.
CPC .......... *A61F 2/2409* (2013.01); *A61F 2/2433* (2013.01); *A61F 2210/0009* (2013.01);
(Continued)

(58) Field of Classification Search
None
See application file for complete search history.

(56) References Cited

U.S. PATENT DOCUMENTS 8,992,604 B2 * 3/2015 Gross .................... A61F 2/2412
623/2.11
9,192,466 B2 * 11/2015 Kovalsky .............. A61F 2/2418
(Continued)

FOREIGN PATENT DOCUMENTS

CN 107847325 A 3/2018
CN 107928841 A 4/2018
(Continued)

OTHER PUBLICATIONS

First office action of prior Chinese patent application No. 202211440667.4 dated Jun. 20, 2023.
(Continued)

*Primary Examiner* — Ann Hu
(74) *Attorney, Agent, or Firm* — Outlier Patent Attorneys, PLLC

(57) ABSTRACT

A split type precisely-anchorable transcatheter valve-in-ring system comprises a split transcatheter valve-in-ring anchoring stent (10) and a transcatheter artificial biological valve-in-ring (20), wherein the shape and structure of the transcatheter valve-in-ring anchoring stent (10) are matched with the real structure of the annuloplasty ring and supravalvular and infravalvular tissues after three-dimensional reconstruction based on imaging data of a patient who have undergone valve failure after implantation of a annuloplasty ring (30), the transcatheter valve-in-ring anchoring stent (10) is firstly delivered to the patient's failed annuloplasty ring for release, deformation and alignment with the supravalvular and infravalvular tissues of the failed annuloplasty ring; the transcatheter artificial biological valve-in-ring (20) is delivered to the transcatheter valve-in-ring anchoring stent (10) for
(Continued)

release, the stent of the transcatheter artificial biological valve-in-ring (20) deforms and expands to the functional state of the transcatheter valve-in-ring, causing the transcatheter valve-in-ring anchoring stent (10) to deform again and combine with the expanded transcatheter valve-in-ring, and meanwhile, the re-deformation of the transcatheter valve-in-ring anchoring stent (10) causes the transcatheter valve-in-ring anchoring stent (10) to combine with the subvalvular structure again and anchor.

24 Claims, 20 Drawing Sheets

(52) U.S. Cl.
CPC ................ *A61F 2210/0014* (2013.01); *A61F 2210/0076* (2013.01); *A61F 2220/0008* (2013.01); *A61F 2230/0067* (2013.01); *A61F 2230/0069* (2013.01); *A61F 2230/0093* (2013.01); *A61F 2240/002* (2013.01); *A61F 2250/006* (2013.01)

(56) References Cited

U.S. PATENT DOCUMENTS

| | | | | |
|---|---|---|---|---|
| 9,326,850 | B2 * | 5/2016 | Venkatasubramanian ................... A61F 2/2418 | |
| 10,052,199 | B2 * | 8/2018 | Spence ................. A61F 2/2418 | |
| 10,245,143 | B2 * | 4/2019 | Gross .................... A61F 2/2439 | |
| 10,376,361 | B2 * | 8/2019 | Gross .................... A61F 2/2436 | |
| 10,588,741 | B2 * | 3/2020 | Zhang ................... A61F 2/2418 | |
| 10,869,756 | B2 * | 12/2020 | Al-Jilaihawi ......... A61F 2/2436 | |
| 11,090,153 | B2 * | 8/2021 | Haarer ................. A61F 2/2418 | |
| 11,213,391 | B2 * | 1/2022 | Ganesan ............... A61F 2/2439 | |
| 11,723,764 | B2 * | 8/2023 | Birmingham ......... A61F 2/2418 623/1.14 | |
| 2006/0271172 | A1 * | 11/2006 | Tehrani ................. A61F 2/2409 623/2.11 | |
| 2010/0076548 | A1 * | 3/2010 | Konno .................. A61F 2/2409 623/2.11 | |
| 2010/0217382 | A1 * | 8/2010 | Chau ..................... A61F 2/2457 623/2.12 | |
| 2011/0137397 | A1 | 6/2011 | Chau et al. | |
| 2014/0005778 | A1 * | 1/2014 | Buchbinder .......... A61F 2/2445 623/2.37 | |
| 2014/0236287 | A1 * | 8/2014 | Clague .................. A61F 2/2436 623/2.11 | |
| 2017/0056162 | A1 | 3/2017 | Harewood et al. | |
| 2017/0281337 | A1 | 10/2017 | Campbell | |
| 2018/0344457 | A1 * | 12/2018 | Gross ...................... A61F 2/246 | |
| 2019/0110893 | A1 | 4/2019 | Haarer et al. | |
| 2019/0343631 | A1 | 11/2019 | Mccarthy | |
| 2021/0154010 | A1 * | 5/2021 | Schneider ............. A61F 2/2436 | |

FOREIGN PATENT DOCUMENTS

| | | |
|---|---|---|
| CN | 110650711 A | 1/2020 |
| CN | 210250166 U | 4/2020 |
| CN | 111447890 A | 7/2020 |
| CN | 214342803 U | 10/2021 |

OTHER PUBLICATIONS

First search report of prior Chinese patent application No. 202211440667.4.

International Search Report of PCT/CN2022/132662 dated Jan. 17, 2023.

Extended European Search Report of counterpart EP application No. 22894922.8 dated Sep. 30, 2025.

\* cited by examiner

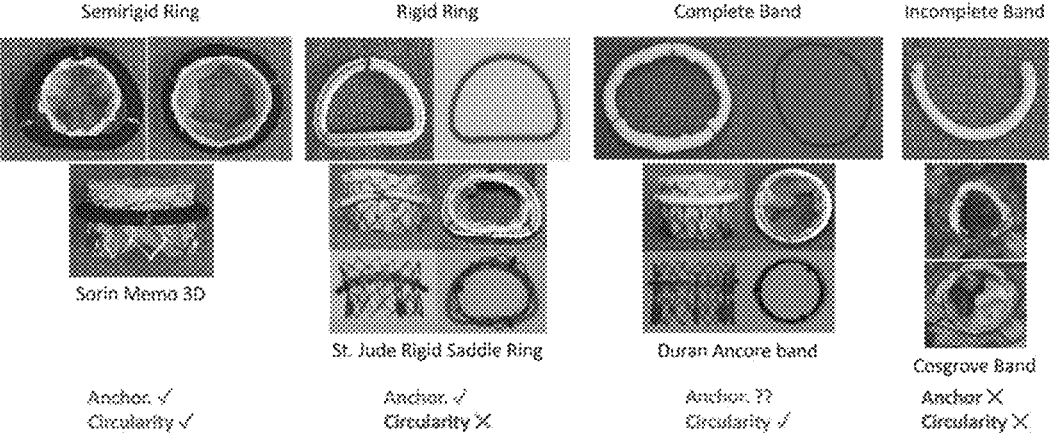
F i g . 1     (Prior Art)
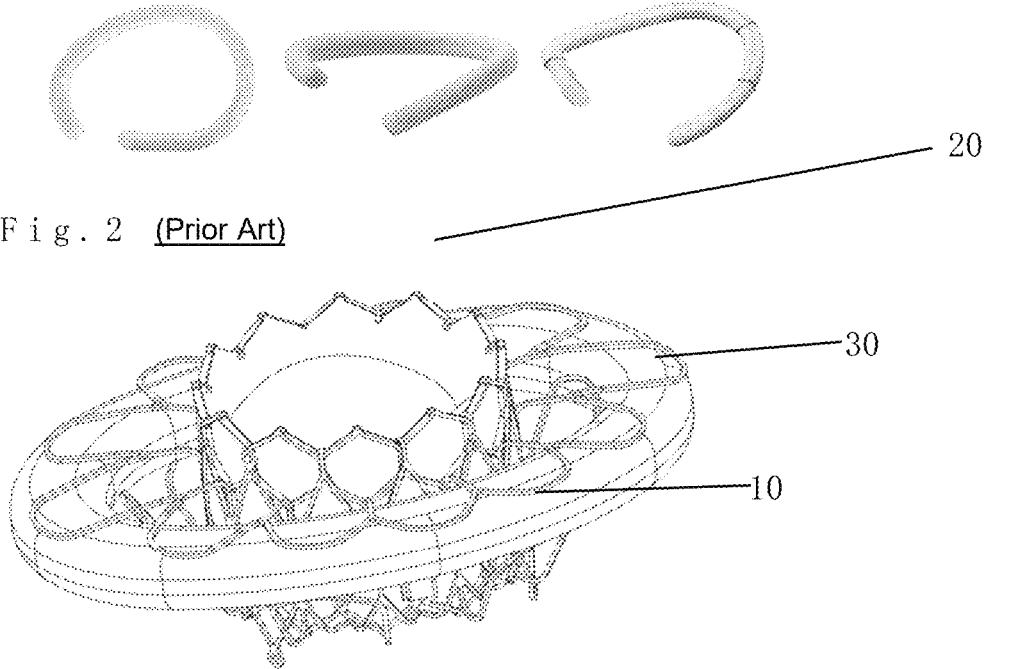
F i g . 2     (Prior Art)
Fig. 3A

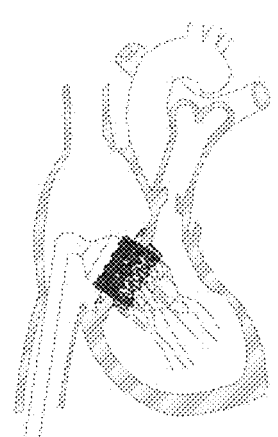
Fig. 23E
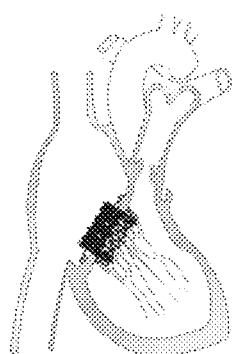
Fig. 23F
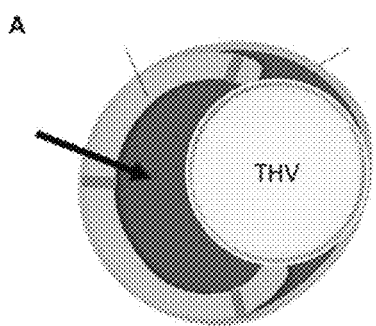
Fig. 24A
Fig. 24B

1

SPLIT TYPE PRECISELY-ANCHORABLE TRANSCATHETER VALVE-IN-RING SYSTEM

CROSS-REFERENCE TO RELATED APPLICATIONS

This application claims priority to International Application No. PCT/CN2022/132662, filed on Nov. 17, 2022, which claims the priority benefit of China Patent Application No. 202111361458.6, filed on Nov. 17, 2021. The contents of the above identified applications are incorporated herein by reference in their entirety.

TECHNICAL FIELD

The invention relates to an artificial biological heart valve, in particular to a split type precisely-anchorable transcatheter valve-in-ring system.

BACKGROUND ART

According to an estimated weighted prevalence rate of 3.8% for valvular heart disease in China, there are approximately 25 million patients with valvular heart disease (BMC Cardiovasc Disorder, 2021, 21:339), and as the majority of domestic patients who require treatment are aged 65 or younger, valve surgery, including artificial valve replacement and valve forming operation repair, should be the main treatment options for a considerable period of time in the future. The former requires the implantation of artificial heart valve, while the latter requires the implantation of annuloplasty rings to complete valve repair. It is estimated that in 2021, approximately 26000 tricuspid annuloplasty rings will be used for tricuspid valve forming surgery, and more than 14000 mitral annuloplasty rings will be used for mitral valve forming surgery, the cumulative number of rings used has significantly exceeded the number of artificial biological valves, and it is still growing in double digits every year. Furthermore, due to the limited time for the popularization and accumulation of surgical experience of valve replacement surgery in China, especially the lower proportion of valve degeneration compared to European and American countries, postoperative patients who undergo valve repair surgery with implanted annuloplasty rings inevitably face valve failure again when they enter advanced age, and thus has to require intervention with the valve-in-ring (ViR) for treatment.

According to a considerable number of literature reports, due to differences in the material, structure, and shape of the previously implanted annuloplasty ring (FIG. 1), compared with the transcatheter valve-in-valve (ViV), the postoperative complications of ViR, as well as the mid postoperative function and quality of life of the valve-in-ring, are far inferior to the treatment effect of ViV. Researchers believe that these issues with ViR mainly stem from the irregularity of the material, shape, and structure of the previously implanted annuloplasty ring, which leads to deformation and inevitable more perivalvular leakage after ViR implantation. For this purpose, the present invention provides a design of a split type transcatheter valve-in-ring system.

SUMMARY

According to the invention, a stable and regular circular support structure is firstly arranged in the mitral annuloplasty ring or the tricuspid annuloplasty ring implanted in the prior art, so that stable and accurate transcatheter anchoring is provided for the valve-in-ring of the balloon expansion. The transcatheter valve-in-ring system of the present invention is composed of two parts: a transcatheter valve-in-ring anchoring stent and a transcatheter artificial biological valve-in-ring, and the core key points of the transcatheter ring valve-in-ring system are as follows: according to the annuloplasty ring and supravalvular and subvalvular real anatomical structures of the three-dimensional reconstruction of pre-operative personalized image data, a device corresponding to the shape, structure, and size of the annuloplasty ring is customized and processed, it can automatically adapt to the annuloplasty ring, and combine and clamp with the supravalvular and subvalvular tissues by positioning and releasing. Subsequently, the transcatheter artificial biological valve-in-ring is delivered through a catheter to the anchoring valve framer for balloon expansion and release, so that the transcatheter valve-in-ring to be assembled and combined with the anchoring stent in vivo, the precise anchoring of the transcatheter valve-in-ring is achieved by aligning the central axis of the anchoring stent connection with the center of the previously implanted annuloplasty ring, in order to achieve accurate anchoring of the transcatheter valve-in-ring, so that the a treatment effect similar to or better than ViV is obtained.

The specific technical scheme adopted by the invention is as follows: a split type precisely-anchorable transcatheter valve-in-ring system comprises a split transcatheter valve-in-ring anchoring stent and a transcatheter artificial biological valve-in-ring, wherein the shape and structure of the transcatheter valve-in-ring anchoring stent are matched with the real structure of the annuloplasty ring and supravalvular and infravalvular tissues after three-dimensional reconstruction based on imaging data of a patient who have undergone valve failure after implantation of a annuloplasty ring, the transcatheter valve-in-ring anchoring stent is firstly delivered to the patient's failed annuloplasty ring for release, deformation and alignment with the supravalvular and infravalvular tissues of the failed annuloplasty ring; the transcatheter artificial biological valve-in-ring is delivered to the transcatheter valve-in-ring anchoring stent for release, the stent of the transcatheter artificial biological valve-in-ring deforms and expands to the functional state of the transcatheter valve-in-ring, causing the transcatheter valve-in-ring anchoring stent to deform again and combine with the expanded transcatheter valve-in-ring, and meanwhile, the re-deformation of the transcatheter valve-in-ring anchoring stent causes the anchoring stent to combine with the subvalvular structure again and anchor.

Further, the re-combining anchor is a preset anchor for achieving precise regular round. The valve-in-ring system further comprising a delivery assembly, wherein the delivery assembly comprises a transcatheter valve-in-ring anchoring stent delivery kit and a transcatheter valve-in-ring delivery kit, and the transcatheter valve-in-ring anchoring stent delivery kit comprises a delivery catheter and a transcatheter valve-in-ring anchoring stent loader. The previously implanted annuloplasty rings refer to various types of mitral annuloplasty rings implanted for various etiologies of mitral valve insufficiency, or various types of tricuspid annuloplasty rings implanted for various etiologies of tricuspid valve insufficiency; the shape and structure of the transcatheter valve-in-ring anchoring stent is accurately matched with the type of annuloplasty ring previously implanted and the personalized imaging data of postoperative valve failure through three-dimensional reconstruction of the real shape and anatomical structure; the transcatheter valve-in-ring anchoring stent and the transcatheter artificial biological valve-in-ring are sequentially inserted, and then reassembled into one in the body, the transcatheter valve-in-ring anchoring stent deforms again due to the release of the transcatheter valve, and completes the predetermined anchoring of the diseased mitral valve or tricuspid valve and subvalvular tissue in a regular circular shape, so that the transcatheter artificial biological valve-in-ring anchoring is protected from the stress of the shape of the previously implanted annuloplasty ring, and the persistent stability of the regular circular anchoring is obtained. The ranscatheter valve-in-ring is a mitral valve-in-ring and a tricuspid valve-in-ring. The transcatheter valve-in-ring anchoring stent has a compressed state disposed in the catheter, a first anchoring state after being released by the catheter, and a second anchoring state after being combined with the transcatheter valve-in-ring, and in the first anchoring state, the valve-in-ring anchoring stent is released from the catheter after being released by the catheter, and is deformed and engaged with the supravalvular and subvalvular tissue of the patient's failed annuloplasty ring; and in the second anchoring state, the valve-in-ring anchoring stent is subjected to secondary deformation via the transcatheter valve-in-ring, and is combined with the transcatheter valve-in-ring to complete the final anchoring and binding to the subvalvular tissue of the patient's failed annuloplasty ring. The transcatheter artificial biological valve-in-ring is delivered by the catheter to the first state of the transcatheter valve-in-ring anchoring stent for balloon expansion and release, the balloon expansion external force causes the valve-in-ring anchoring stent to deform again, and it combines with the expanded transcatheter artificial biological valve-in-ring to form a body, to realize the preset anchoring of the anchoring stent with the valve leaflet and subvalvular tissue of the patient's mitral or tricuspid valve site in a preset circular shape. In the first anchoring state, the transcatheter valve-in-ring anchoring stent is processed and shaped into a conical funnel shape with a large atrial surface and a small ventricular surface according to the type, shape and size of the implanted annuloplasty ring and the personalized image data after three-dimensional reconstruction, the transcatheter valve-in-ring anchoring stent is input and released through the catheter and is adapted to adapt to the supravalvular and subvalvular tissue of the patient's failed mitral valve or tricuspid valve to perform personalized alignment bonding and docking to form a preset structure with a circular shape in a remodeling rule; and in the second anchoring state, in the transcatheter valve-in-ring anchoring stent of the first anchoring state, the transcatheter artificial biological valve-in-ring is delivered through the catheter and is released by the balloon expansion, and is combined with the transcatheter valve-in-ring anchoring stent to form a whole, so that the transcatheter valve-in-ring anchoring stent is expanded from the original conical funnel shape to a cylindrical shape together with transcatheter valve-in-ring, and the centripetal return clip generated by the secondary deformation is tightly combined with the v transcatheter valve-in-ring to complete the preset anchoring with the mitral valve site or the tricuspid valve site and the subvalvular tissue of the patient.

Further, the real structure of the three-dimensional reconstruction is a digital image model or a three-dimensional printed simulation entity model, and the real structure of the three-dimensional reconstruction is a virtual simulated three-dimensional image and corresponding three-dimensional printed simulated entity model after the digital conversion of CT, ultrasound, and MRI comprehensive images. The valve-in-ring anchoring stent is an umbrella tubular stent structure, comprising an atrial surface, a ventricular surface, and an anchoring stent connecting part therebetween, and the anchoring stent connecting part therebetween, wherein the atrial surface is an umbrella shape and has an umbrella shape matching with the real shape of the three-dimensional reconstruction of the atrial surface image data of the patient, which is a first lattice portion; the ventricular surface is a plurality of positioning hook loops precisely aligned with the leaflet boundary; the anchoring stent connecting part is a round opening funnel shape and has a second lattice portion. The first anchoring state of the connecting part of the valve-in-ring anchoring stent is a shape-setting memory state in vitro of the stent after being delivered and released through the catheter, the shape-setting memory state of the connecting part from the atrial surface to the ventricular surface has a contraction taper, with a taper of 5-45 degrees; the connecting part of the anchoring stent undergoes deformation and expansion, transforming from a first anchoring state to a cylindrical second anchoring state. The positioning hook loop is a precise alignment match between two leaflets of the patient's mitral valve (mitral annuloplasty ring) or three leaflets of the tricuspid valve (tricuspid annuloplasty ring). In the first anchoring state of the transcatheter valve-in-ring anchoring stent, the positioning hook loop is released through the catheter in advance of the atrial surface of the transcatheter valve-in-ring anchoring stent, and the valve leaflet junction position of the patient's mitral valve or tricuspid valve matched with the positioning hook loop is inserted, so that the atrial surface of the positioning anchoring stent matches with the atrial shape of the patient; in the second anchoring state after the transcatheter valve-in-ring anchoring stent is deformed, the positioning hook loop and the periphery of the connecting part of the anchoring stent are filled between a coupling portion of the annuloplasty ring and the transcatheter valve-in-ring. In the second anchoring state, the positioning hook loop is filled in the eccentric region of the previously implanted annuloplasty ring, so that the central axis of the connecting part of the valve-in-ring anchoring stent is coaxial with the center of the previously implanted annuloplasty rings. The ventricular surface of the valve-in-ring anchoring stent has a plurality of anchoring hook loops, which extend from the connecting part to the ventricular surface and then are folded, so as to match with the shape of real subvalvular tissue of the three-dimensional reconstruction of the subvalvular image data of the patient's failed valve. In the first anchoring state of the valve-in-ring anchoring stent, after the anchoring hook loop is released through the catheter, the anchoring hook loop is aligned with the subvalvular tissue of the patient's failed annuloplasty ring, and in the second anchoring state of the valve-in-ring anchoring stent, the plurality of anchoring hook loops form the clamping portion by action of deformation and the resultant force of the atrial surface and the connecting part of the valve-in-ring anchoring stent, and the plurality of deformed anchoring hook loops are tightly combined with the leaflet and subvalvular tissue under the patient's failed annuloplasty ring. The anchoring hook loop is 2-9, preferably 4-6. The atrial surface end portion of the connecting part of the valve-in-ring anchoring stent is provided with a plurality of fixed support rods or stent bending for embedding the transcatheter valve-in-ring stent, the fixed support rod or stent bending is extended in the axial direction of the atrial surface, and the ends thereof are bent towards the axis of the anchoring stent. The connecting part of the valve-in-ring anchoring stent is provided with a plurality of end centripetal bending portions for embedding the outflow end of the transcatheter valve-in-ring stent, and the atrial surface end portions of the connecting parts of the centripetal bending and ring valve-in-ring anchoring stent are provided with a plurality of fixed support rods or bending upper and lower commissures for embedding the atrial end of the transcatheter valve-in-ring stent and to form an integrated whole with the anchoring stent, ensuring that the transcatheter valve-in-ring releases zero displacement. The fixed support rod or stent bending is 3-12, preferably 6-9. The first lattice portion and the second lattice portion of the valve-in-ring anchoring stent are formed by a unit lattice composed of a compressible rhombic lattice, a V-shaped lattice and/or a hexagonal or polygonal lattice, and the first lattice portion is adaptively connected to the second lattice portion. An outer periphery of the lattice portion of the atrial surface is spaced 1-2 mm from an atrial wall of the patient, preferably 1.5 mm apart. An inner peripheral edge diameter of the second lattice portion matches an outer diameter of various corresponding size specifications of a transcatheter artificial biological valve-in-ring. A layer of medical polymer film is coated on the surface of the valve-in-ring anchoring stent. The connecting parts of the atrial surface, the ventricular surface and the anchoring stent of the valve-in-ring anchoring stent are three-dimensional forming structures or split connecting structures after laser integrated cutting. The anchoring stent is a metallic material or a non-metallic material having shape-setting memory properties, and the anchoring stent is made of a nickel-titanium alloy material. The transcatheter artificial biological valve-in-ring comprises a cobalt-chromium alloy stent which is radially compressible and can be expanded by a balloon and is in a cylindrical shape, or a nickel-titanium alloy stent which is radially compressible and self-expandable and has a cylindrical shape, and three fan-shaped leaflets arranged on the inner side of the stent, wherein the three fan-shaped leaflets each have a free edge, an arc-shaped bottom edge and leaflet boundary connecting parts which extend on the two sides, and the stent is a metal net tube. The valve frame is a cobalt-based alloy cobalt or chromium alloy or a nickel-titanium alloy. The transcatheter valve-in-ring anchoring stent delivery device and the transcatheter artificial biological valve-in-ring delivery device, for the tricuspid valve-in-ring, it can be approached from the inferior vena cava via the femoral vein, or from the superior vena cava via the jugular vein or subclavian vein to the tricuspid valve site; and for the mitral valve-in-ring, it can be approached through the apex of the heart, left atrium, or femoral vein via the interventricular septum to the mitral valve site.

In the invention, each completion of the transcatheter valve-in-ring treatment process for realizing precise shaping and anchoring for personalized preset, all of the related data are used as independent data units, a large amount of personalized data units are accumulated, and intelligent, large-scale and industrialization of the split type precisely-anchorable transcatheter valve-in-ring system is realized through an algorithm of big data and AI.

BRIEF DESCRIPTION OF DRAWINGS

FIG. 1 shows a physical image of different types of mitral annuloplasty rings and tricuspid annuloplasty rings implanted in the prior art.

FIG. 2 shows a physical image of various annuloplasty rings in the prior art.

6

Figure 3B:
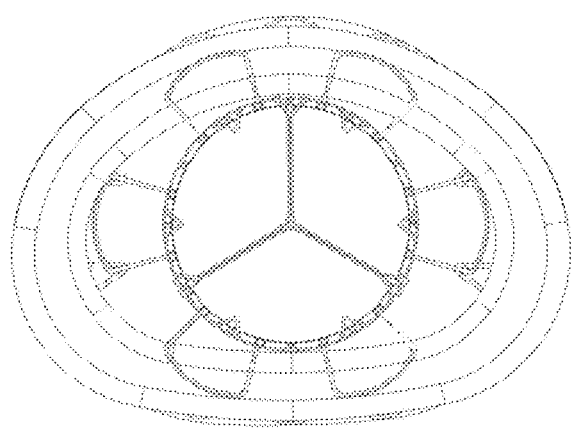

FIGS. 3A-B show a schematic diagram of the implantation of the annuloplasty ring in a transcatheter valve-in-ring system according to an embodiment of the present invention.

Figure 4:
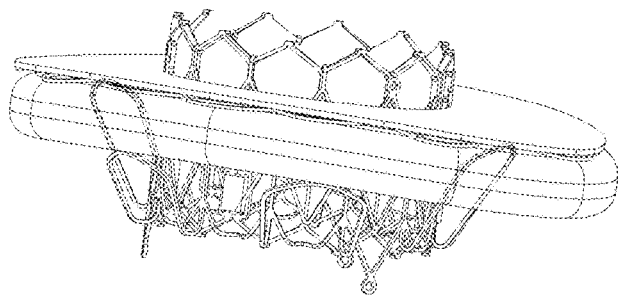

FIG. 4 shows a schematic diagram of implantation and formation of a transcatheter valve-in-ring system according to an embodiment of the present disclosure.

Figure 5:
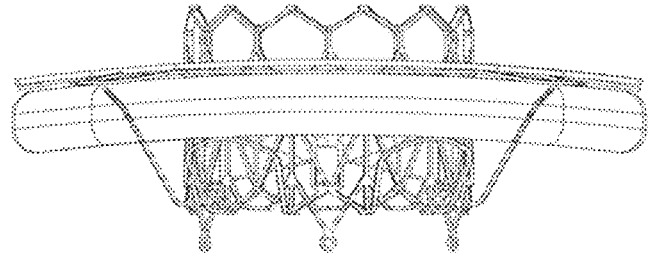

FIG. 5 shows a schematic diagram of implantation and formation of a transcatheter valve-in-ring system according to an embodiment of the present disclosure.

Figure 6:
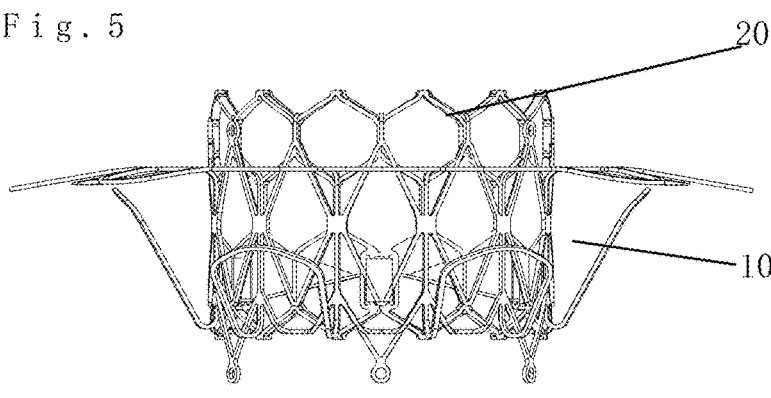

FIG. 6 shows a schematic diagram of a transcatheter valve-in-ring system according to an embodiment of the present disclosure.

Figure 7:
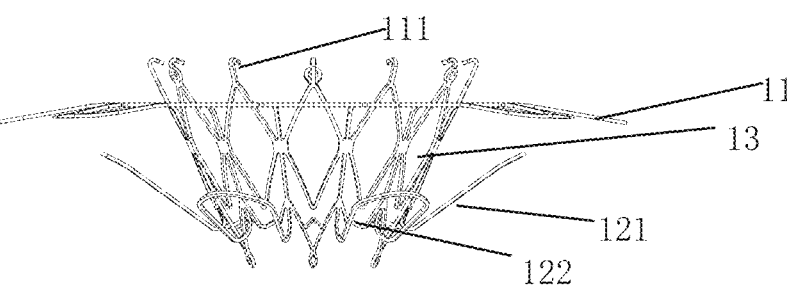

FIG. 7 shows a schematic diagram of a transcatheter valve-in-ring anchoring stent according to an embodiment of the present disclosure.

Figure 8:
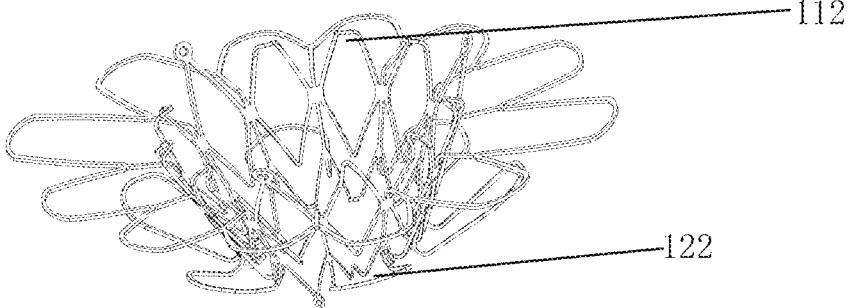
Figure 9:
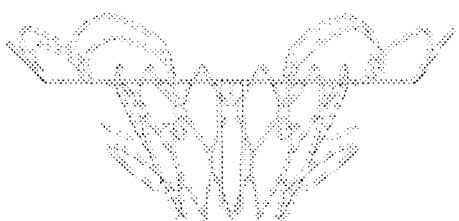
Figure 10:

FIG. 8-10 show a schematic diagram of a transcatheter valve-in-ring anchoring stent with different shapes according to an embodiment of the present disclosure.

Figure 11A:
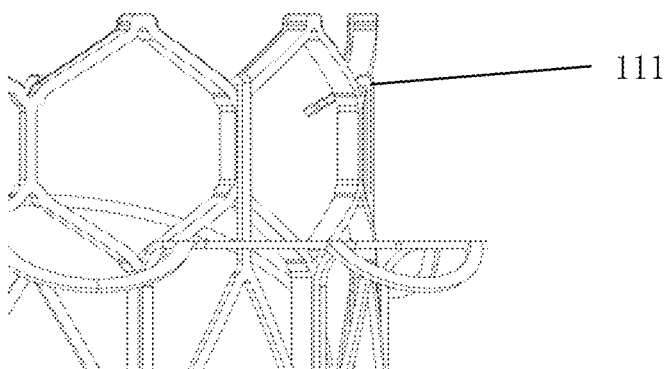
Figure 11B:
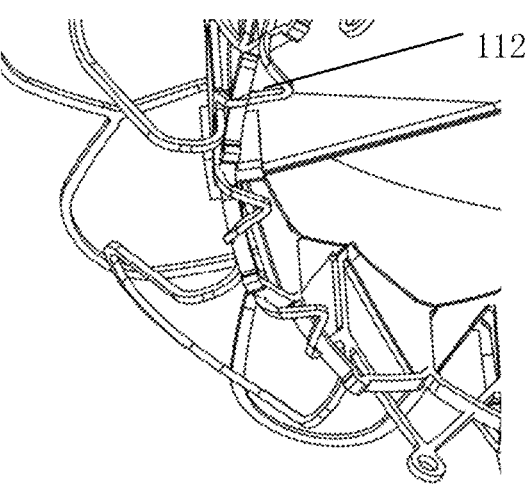

FIGS. 11A-B show a schematic diagram of fixed support rods and centripetal bending of an anchoring stent according to an embodiment of the present disclosure.

Figure 12A:
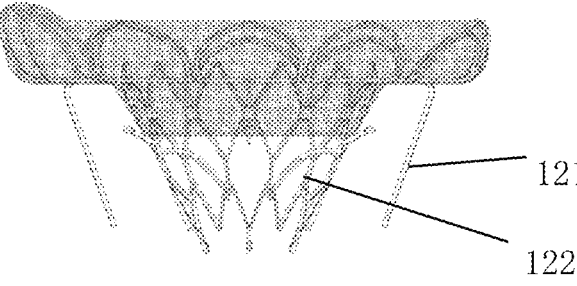
Figure 12B:
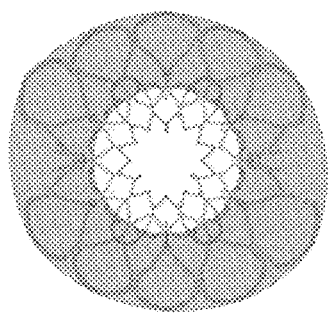
Figure 12C:
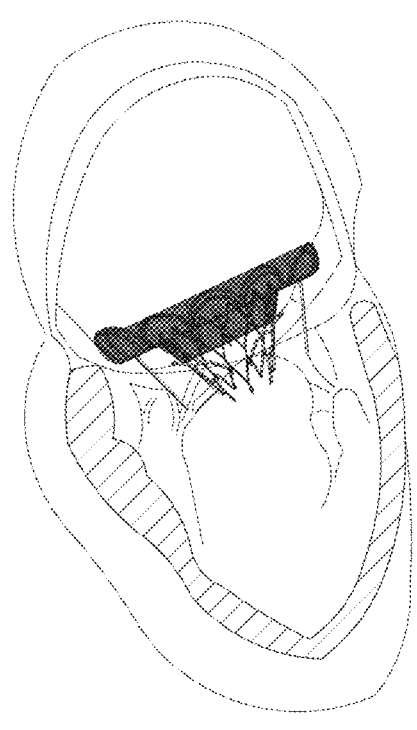

FIG. 12A-C show a schematic diagram of a first anchoring state of a transcatheter valve-in-ring anchoring stent according to an embodiment of the present disclosure.

Figure 13A:
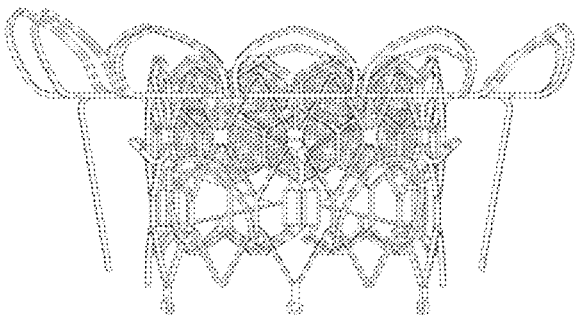
Figure 13B:
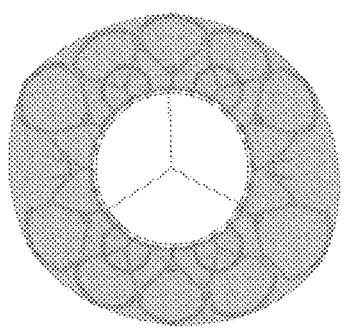
Figure 13C:
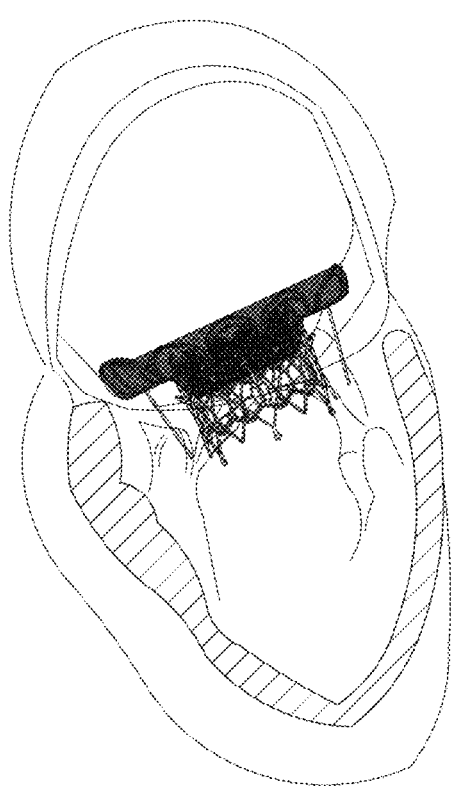

FIG. 13A-C show a schematic diagram of a second anchoring state of a transcatheter valve-in-ring anchoring stent according to an embodiment of the present disclosure.

Figure 14:
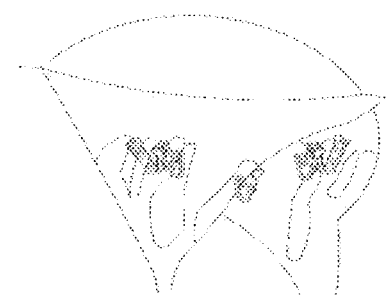

FIG. 14 shows a schematic diagram of anchoring hook loops and chordae tendineae secondary anchoring after a transcatheter mitral valve anchoring stent is implanted into a human body according to an embodiment of the present disclosure.

Figure 15:
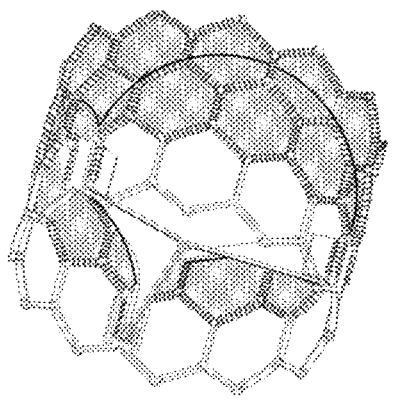

FIG. 15 shows a schematic diagram of a transcatheter artificial biological valve-in-ring according to an embodiment of the present disclosure.

Figure 16:
Figure 17A:
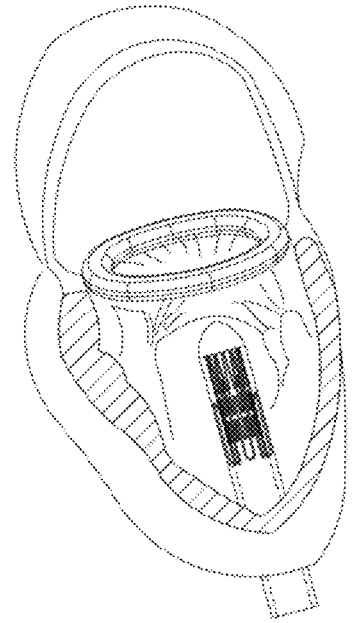
Figure 17B:
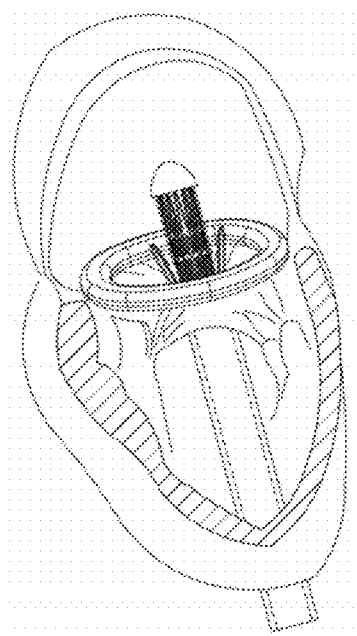
Figure 17C:
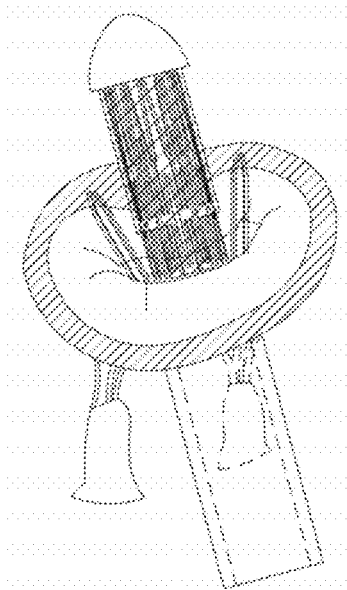
Figure 17D:
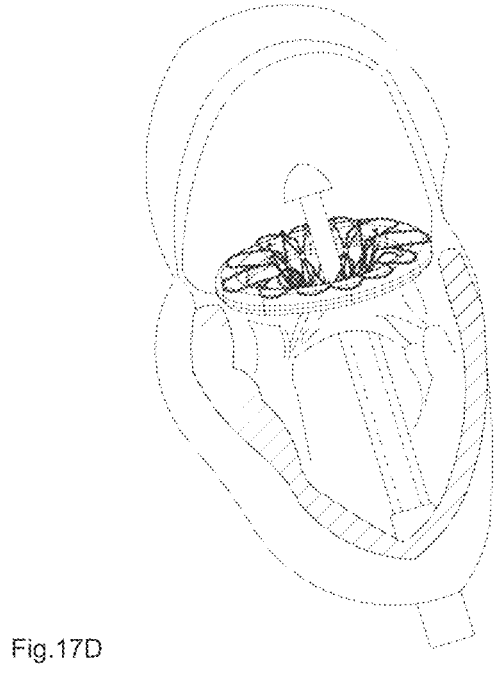
Figure 17E:
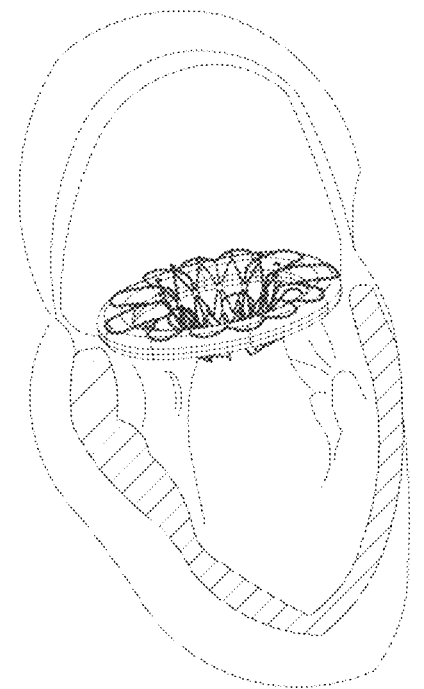

FIG. 16 shows a schematic diagram of a delivery system according to an embodiment of the present disclosure.

FIG. 17A-E show a schematic diagram of a process of anchoring a stent in a transcatheter valve-in-ring through the apical approach according to an embodiment of the present invention.

Figure 18A:
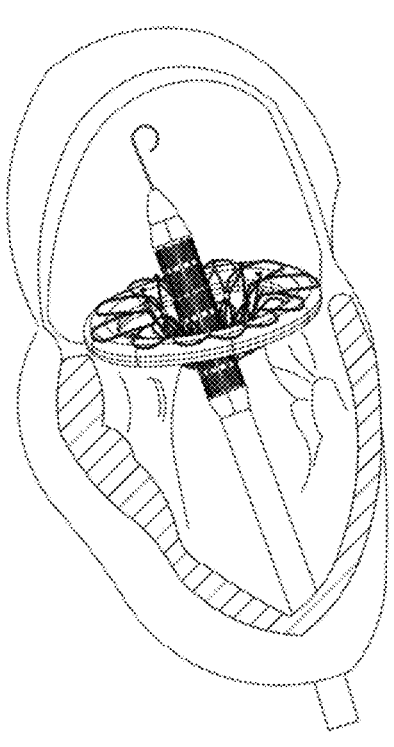
Figure 18B:
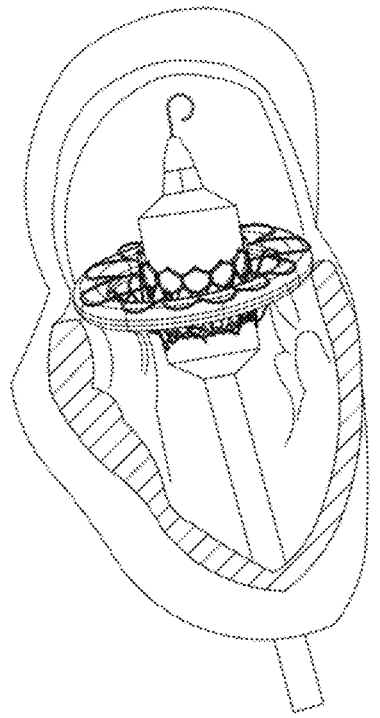
Figure 18C:
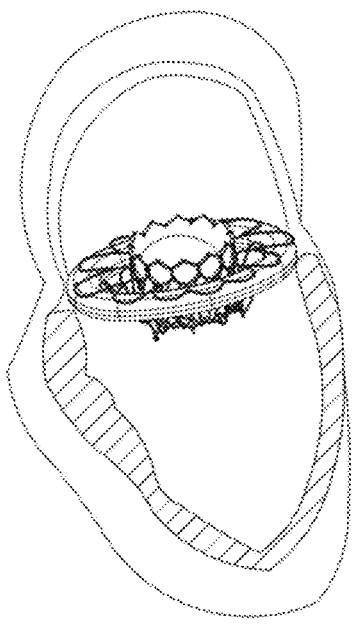
Figure 19A:
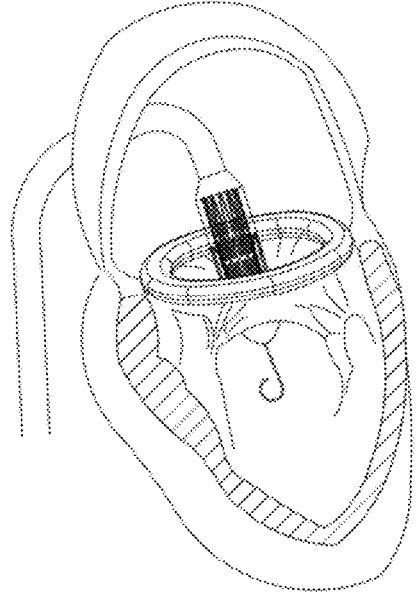
Figure 19B:
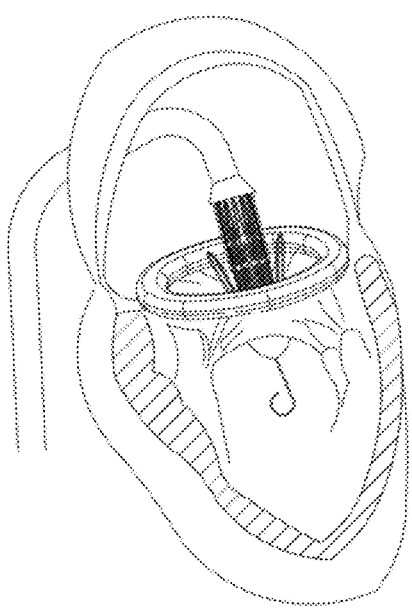
Figure 19C:
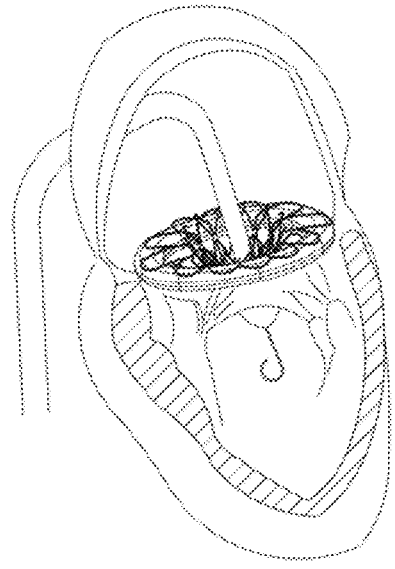
Figure 19D:
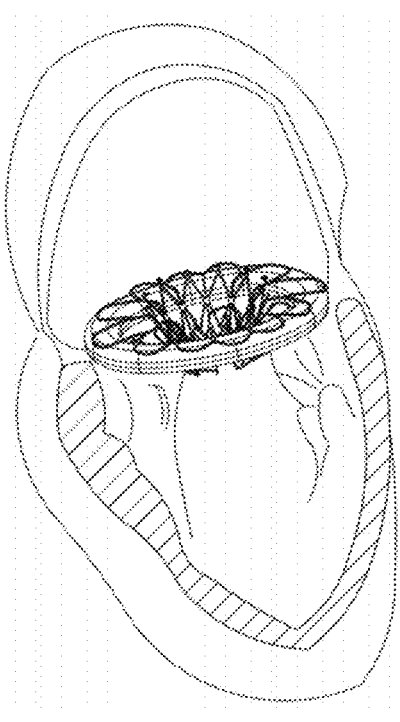

FIG. 18A-C show a schematic diagram of a process of delivering and anchoring a stent in a transcatheter valve-in-ring through the apical approach according to an embodiment of the present invention.

FIG. 19A-D show a schematic diagram of a process of anchoring a stent in a transcatheter valve-in-ring through atrial septum by a transfemoral approach according to an embodiment of the present invention.

Figure 20A:
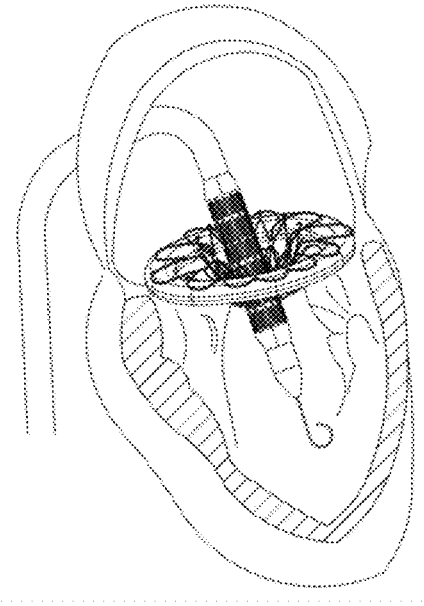
Figure 20B:
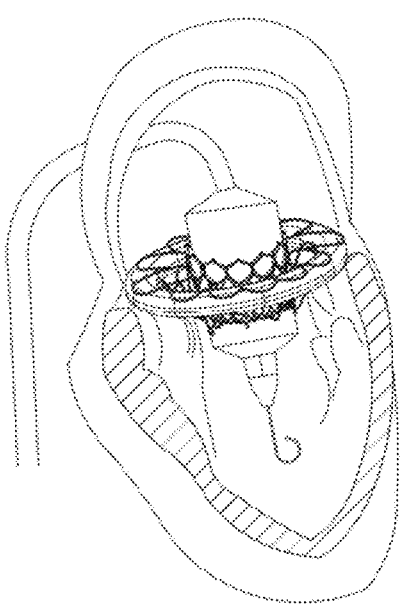
Figure 20C:
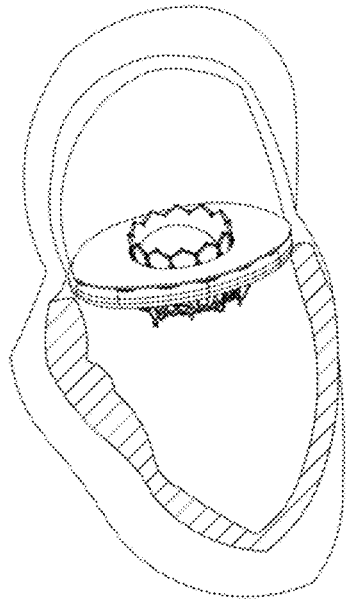

FIG. 20A-C show a schematic diagram of a process of feeding a transcatheter valve-in-ring through atrial septum into an anchoring stent by a transfemoral approach according to an embodiment of the present invention.

Figure 21A:
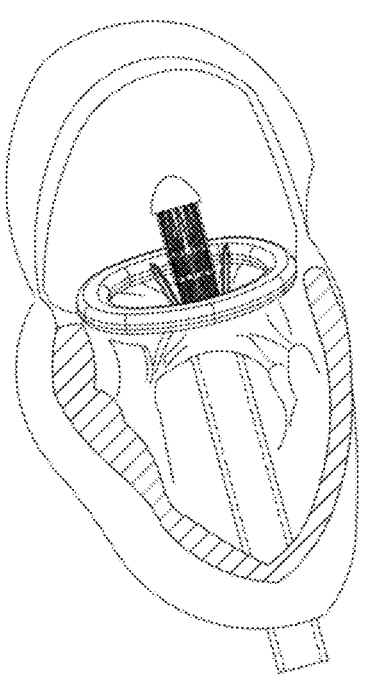
Figure 21B:
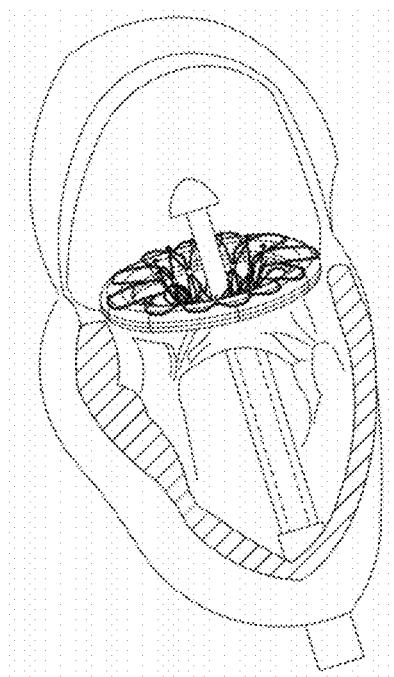
Figure 21C:
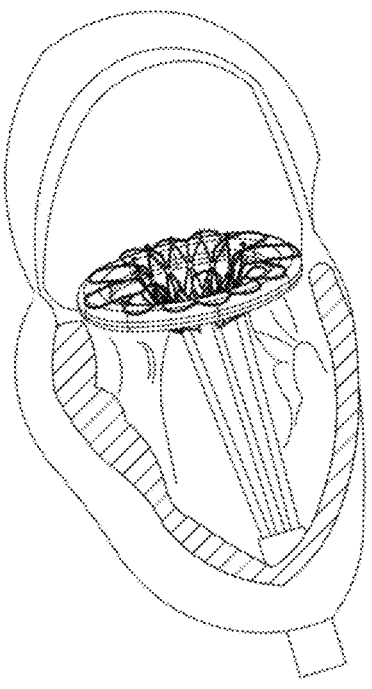
Figure 22A:
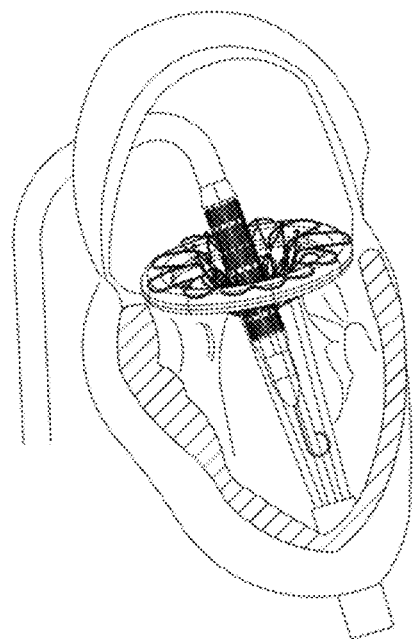
Figure 22B:
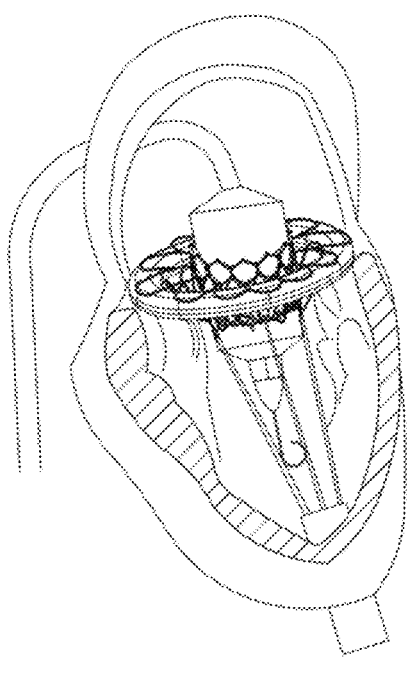
Figure 22C:
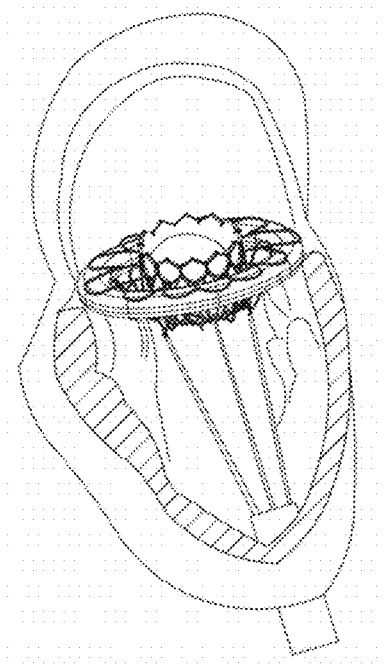
Figure 22D:
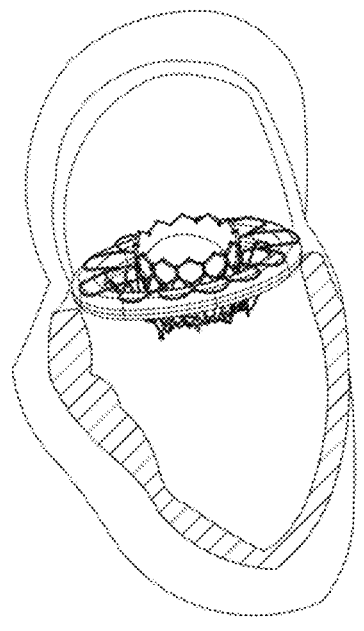
Figure 23A:
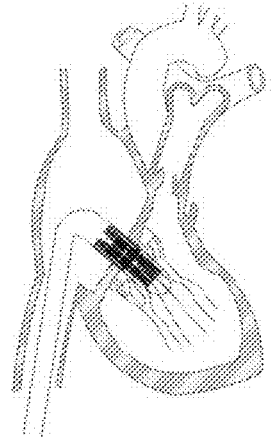
Figure 23B:
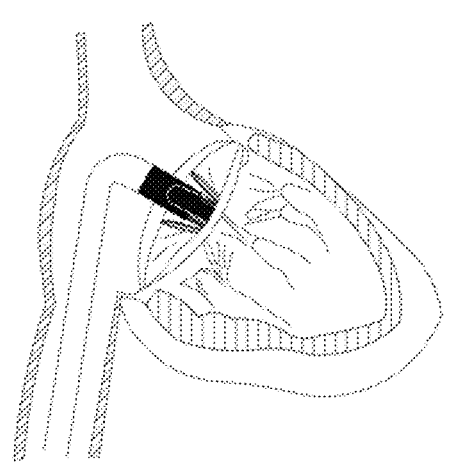
Figure 23C:
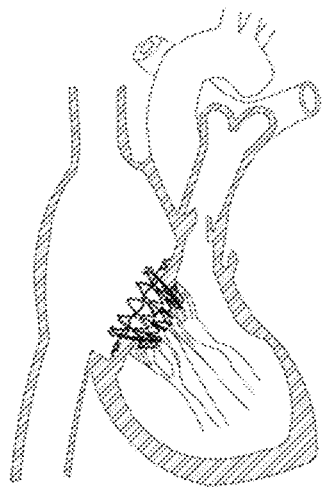
Figure 23D:
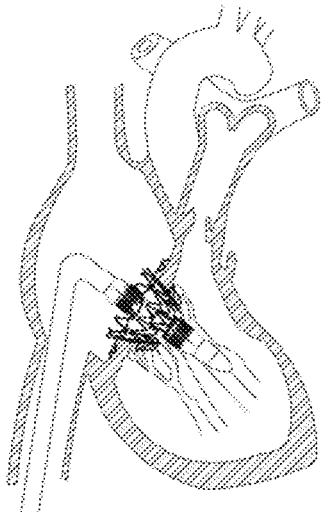

FIG. 21A-C show a schematic diagram of a process of introducing a composite approach into a transcatheter valve-in-ring anchoring stent according to an embodiment of the present invention.

FIGS. 22A-D show a schematic diagram of a process of feeding a transcatheter valve-in-ring into an anchoring stent via a composite approach according to an embodiment of the present invention.

FIG. 23A-F show a schematic diagram of the tricuspid valve site intervention in the valve-in-ring system of this application according to the embodiment of the present invention.

FIG. 24A-B show a schematic diagram of a positioning hook loop of the anchoring stent filled in the eccentric area of the previously implanted annuloplasty ring according to an embodiment of the present invention.

DETAILED DESCRIPTION

Referring to FIG. 3 to FIG. 6, the split type precisely-anchorable transcatheter valve-in-ring system of the present invention comprises a split transcatheter valve-in-ring anchoring stent 10 and a transcatheter artificial biological valve-in-ring 20, wherein the shape and structure of the transcatheter valve-in-ring anchoring stent are matched with the real structure of the annuloplasty ring and supravalvular and infravalvular tissues after three-dimensional reconstruction based on imaging data of a patient who have undergone valve failure after implantation of a annuloplasty ring 30, the transcatheter valve-in-ring anchoring stent is firstly delivered to the patient's failed annuloplasty ring for release, deformation and alignment with the supravalvular and infra-valvular tissues of the failed annuloplasty ring; the trans-catheter artificial biological valve-in-ring is delivered to the transcatheter valve-in-ring anchoring stent for release, the stent of the transcatheter artificial biological valve-in-ring deforms and expands to the functional state of the trans-catheter valve-in-ring, causing the transcatheter valve-in-ring anchoring stent to deform again and combine with the expanded transcatheter valve-in-ring, and meanwhile, the re-deformation of the transcatheter valve-in-ring anchoring stent causes the anchoring stent to combine with the sub-valvular structure again and anchor.

Referring to FIG. 7 to FIG. 13, the transcatheter valve-in-ring anchoring stent is one of the key components of the transcatheter valve-in-ring system of the present invention, the valve-in-ring anchoring stent is an umbrella tubular stent structure, comprising an atrial surface 11, a ventricular surface 12, and an anchoring stent connecting part 13 therebetween, and the anchoring stent connecting part ther-ebetween, wherein the atrial surface is an umbrella shape and has an umbrella shape matching with the real shape of the three-dimensional reconstruction of the atrial surface image data of the patient, which is a first lattice portion; the ventricular surface is positioning hook loops 121; the posi-tioning hook loop is a precise alignment match between two leaflets of the patient's mitral valve (mitral annuloplasty ring) or three leaflets of the tricuspid valve (tricuspid annu-loplasty ring); the anchoring stent connecting part is a round opening funnel shape and has a second lattice portion. The first anchoring state of the connecting part of the valve-in-ring anchoring stent is a shape-setting memory state in vitro of the stent after being delivered and released through the catheter, the shape-setting memory state of the connecting part from the atrial surface to the ventricular surface has a contraction taper, with a taper of 5-45 degrees; the connect-ing part of the anchoring stent undergoes deformation and expansion, transforming from a first anchoring state to a cylindrical second anchoring state. In the first anchoring state of the transcatheter valve-in-ring anchoring stent, the positioning hook loop is released through the catheter in advance of the atrial surface of the transcatheter valve-in-ring anchoring stent, and the valve leaflet junction position of the patient's mitral valve or tricuspid valve matched with the positioning hook loop is inserted, so that the atrial surface of the positioning anchoring stent matches with the atrial shape of the patient; in the second anchoring state after the transcatheter valve-in-ring anchoring stent is deformed, the positioning hook loop and the periphery of the connecting part of the anchoring stent are filled between a coupling portion of the annuloplasty ring and the transcatheter valve-in-ring. In the second anchoring state, the positioning hook loop is filled in the eccentric region of the previously implanted annuloplasty ring, so that the central axis of the connecting part of the valve-in-ring anchoring stent is coaxial with the center of the previously implanted annulo-plasty rings. The ventricular surface of the valve-in-ring anchoring stent has a plurality of anchoring hook loops 122, which extend from the connecting part to the ventricular surface and then are folded, so as to match with the shape of real subvalvular tissue of the three-dimensional reconstruc-tion of the subvalvular image data of the patient's failed valve. In the first anchoring state of the valve-in-ring anchor-ing stent, after the anchoring hook loop is released through the catheter, the anchoring hook loop is aligned with the subvalvular tissue of the patient's failed annuloplasty ring, and in the second anchoring state of the valve-in-ring anchoring stent, the plurality of anchoring hook loops form the clamping portion by action of deformation and the resultant force of the atrial surface and the connecting part of the valve-in-ring anchoring stent, and the plurality of deformed anchoring hook loops are tightly combined with the leaflet and subvalvular tissue under the patient's failed annuloplasty ring.

The shape and coverage area of the atrial surface, as well as the shape, quantity, length, angle, and structural relation-ship of the stent ventricular surface and anchoring hook loop 122, of the transcatheter valve-in-ring anchoring stent are all based on the preoperative CT and ultrasound image data of the patient, and after three-dimensional reconstruction (3mensio), the real structure of the patient's atrium (above the valve) and ventricle (below the valve), as well as the measured real size and structure of each diameter limit, are accurately matched. Based on this, a processing drawing of the transcatheter valve-in-ring anchoring stent is made, and through specific nickel titanium memory alloy tube laser cutting and three-dimensional forming processing, the per-sonalized valve-in-ring anchoring stent is finally custom-ized.

The above process and manufacture of the valve-in-ring anchoring stent based on patient's imaging real data is the state before the stent is pressed, and it is also the first anchoring state after the stent is delivered to the annulo-plasty ring through the catheter and released. The second anchoring state of the transcatheter valve-in-ring anchoring stent is when the transcatheter valve-in-ring is delivered to the anchoring stent through the catheter, and with the assistance of balloon dilation, the valve is expanded, causing the valve-in-ring anchoring stent to deform from the first anchoring state to the second anchoring state. By combining the deformation force of the stent with the balloon expansion force released by the transcatheter valve-in-ring, it becomes one entity. And meanwhile, several anchoring hook loops 122 are inserted into the ventricular surface of the subval-vular anchoring stent, and automatically adapt to the chor-dae tendineae gape and subvalvular tissue as the heart shrinks. Under the external force of the balloon expansion in the transcatheter valve-in-ring, as the anchoring stent is transformed from the first anchoring state to the second anchoring state, the anchoring stent is tightly combined with the chordae tendineae and subvalvular tissue to achieve final anchoring. At the same time, in the first anchoring state of the anchoring stent, the connecting structure of the atrium end fixed support rod deforms to the second anchoring state. The fixed support rod 111 is axially parallel to the center, so that the end of the fixed support rod and the bending hook 112 of the connecting part ventricular end are combined to grip the support rods at both ends of the stent of the transcatheter valve-in-ring. This anchoring stent and the automatic interlocking structure at both ends of the valve apex of the transcatheter valve-in-ring accurately combine the transcatheter valve-in-ring with the anchoring stent, ensuring zero displacement of the transcatheter valve-in-ring.

According to the split type precisely-anchorable transcatheter valve-in-ring system of the invention, the transcatheter artificial biological valve-in-ring, due to the combination of anchoring stents, only serves the reasonable support of the three leaflets in the valve frame structure, and the transcatheter artificial biological valve-in-ring comprises a cobalt-chromium alloy stent which is radially compressible and can be expanded by a balloon and is in a cylindrical shape, or a nickel-titanium alloy stent which is radially compressible and self-expandable and has a cylindrical shape, and three fan-shaped leaflets arranged on the inner side of the stent, wherein the three fan-shaped leaflets each have a free edge, an arc-shaped bottom edge and leaflet boundary connecting parts which extend on the two sides, and the stent is a metal net tube or various forms of compressible stents that can support and fix the junction of the three leaflets. The valve frame is a cobalt-based alloy cobalt or chromium alloy or a nickel-titanium alloy.

The split type precise anchoring intervention ring valve-in-ring system of the invention further comprises a delivery assembly, wherein the delivery assembly comprises a transcatheter valve-in-ring anchoring stent delivery kit and a transcatheter valve-in-ring delivery kit, and the transcatheter valve-in-ring anchoring stent delivery kit comprises a delivery catheter and a transcatheter valve-in-ring anchoring stent loader. The transcatheter artificial biological valve-in-ring delivery kit comprises a transcatheter artificial biological valve-in-ring delivery device, a guide sheath, a valve holder, and a charging pump. The transcatheter valve-in-ring anchoring stent delivery device and the transcatheter artificial biological valve-in-ring delivery device can be used to treat mitral valve dysfunction in patients after mitral valve reconstruction through the femoral vein through the atrial septum, apex puncture, or left atrial puncture approach; ViR treatment can also be performed through the inferior vena cava via the femoral vein, or through the superior vena cava via the jugular or subclavian vein for patients with tricuspid valve failure after tricuspid valve reconstruction surgery.

The invention is summarized as follows: $\hat{1}$ the split anchoring stent design and the transcatheter valve-in-ring are respectively inserted and then assembled and combined in the heart; $\hat{2}$ according to the three-dimensional real form and structure reconstructed by the pre-operative personalized annuloplasty ring and the supravalvular and subvalvular structure image data, the anchoring stent with the specific form structure is designed and processed in a personalized design and processing; $\hat{3}$ by using the valve leaflet boundary, the atrial surface of the anchoring stent is accurately positioned and filled with the inner edge of the irregular annuloplasty ring through the special positioning hook loop, and a regular circular anchor support structure is constructed manually; $\hat{4}$ the transcatheter valve-in-ring is introduced into the anchoring stent in the first anchoring state to be released, the anchoring stent is deformed into the second anchoring state through the balloon expansion external force released by the transcatheter valve-in-ring, the transcatheter valve-in-ring can be integrally combined with the anchoring stent in the second anchoring state in the annuloplasty ring, and meanwhile, the subvalvular tissue is fastened again, and the circular anchor of the final stability rule is completed; $\hat{5}$ the first state deformation after release of the anchoring stent is automatically and adaptively inserted along with the diastolic contraction of the heart, and the personalized anatomy is smoothly engaged, griped and clamped; in the second state, the release control of the transcatheter valve-in-ring is realized through the deformation process embedded in the inner leaflet of the transcatheter valve-in-ring by means of the balloon expansion surgical phase, so that automatic precise and zero displacement is achieved.

Specifically, the technical solution and implementation method adopted by the present invention are:

1. Implementation Example of Mitral Valve Site $\hat{1}$ the Transapical Approach (See FIGS. 17-18)

The transapical approach is often a familiar implementation method for cardiac surgeons. Firstly, the loaded anchoring stent is delivered into the patient's failed mitral valve through the transapical approach, the positioning hook loop is released, and positioning is completed; the atrial surface, the stent connecting structure and the ventricular surface of the anchoring stent are released in sequence, and the ventricular surface anchoring hook loop is aligned and combined; the anchoring stent delivery device is withdrawn, the pre-loaded transcatheter valve-in-ring is delivered to the anchoring stent along the original path, then the transcatheter valve-in-ring is expanded through balloon assistance, the anchoring stent is deformed into the second anchoring state, the anchoring stent is automatically and accurately combined with the transcatheter valve-in-ring, and meanwhile, the anchoring stent is buckled with the inferior tissue to complete final anchoring.

$\hat{2}$) the Transfemoral Approach into the Right Atrium Through Atrial Septum (See FIGS. 19-20).

The transfemoral approach through atrial septum is a familiar implementation method for cardiologists. Insert the loaded anchoring stent into the right atrium through the femoral vein and the inferior vena cava, and then through the interventricular septum into the patient's failed mitral annuloplasty ring, and the positioning hook loop is released to complete positioning, the anchoring stent is sequentially released on the ventricular surface, the stent connection structure, and the atrial surface, so that the anchoring hook loop on the ventricular surface is aligned and combined, which is the first anchoring state of the anchoring stent; the anchoring stent delivery device is withdrawn, the loaded transcatheter valve-in-ring is delivered into the anchoring stent along the original path, then the transcatheter valve-in-ring is expanded by balloon assistance, the anchoring stent is deformed into the second anchoring state, the anchoring stent is accurately combined with the transcatheter valve-in-ring, and meanwhile, the anchoring stent is clamped with the subvalvular tissue to complete final anchoring.

$\hat{3}$ the Composite Approach is Referred to FIGS. 21-22.

The composite approach is suitable for cases where preoperative imaging analysis of the heart structure is complex, and the first state anchoring alignment of the designed transcatheter anchoring stent is uncertain in terms of its firmness. Insert the loaded anchoring stent into the patient's failed mitral valve through the transapical approach, release the positioning hook loop for positioning, sequentially release the atrial surface and connecting part of the anchoring stent, and then release the ventricular surface of the anchoring stent to align the anchoring hook loop, which is the first state of the anchoring stent, the anchoring stent delivery device is not withdrawn to pull the anchoring stent; then, the transcatheter mitral valve loaded with the transcatheter mitral valve is delivered into the anchoring stent through atrial septum at the same time, the transcatheter mitral valve is expanded through balloon assistance, the anchoring stent is deformed into the second anchoring state, the anchoring stent is accurately combined with the transcatheter mitral valve, and meanwhile, the anchoring stent is clamped with the inferior tissue to complete final anchoring; the transcatheter mitral valve transporter is withdrawn, the second anchoring state of the anchoring stent is confirmed to be in a designed state, and the anchoring stent delivery device is withdrawn after anchoring is firm.

The most common approach for the implementation of the tricuspid valve system is through the femoral vein from the inferior vena cava to the right atrium to reach the tricuspid valve position. The implementation example is the same as the approach for the mitral valve position $\hat{2}$ through the femoral vein from the right atrium through the atrial septum, and through the femoral vein to the right atrium, as shown in FIG. 23.

The transcatheter valve-in-ring system of the present invention has performed the above technical solutions in animal experiments, and it has been confirmed that it is feasible.

The invention has the significance that: the significance of the present invention lies in: $\hat{1}$ the split type design, which hands the anchoring of the valve to a precisely designed anchoring stent, so that the stent of the transcatheter valve-in-ring is only responsible for symmetrical support of the three valve leaflets, providing the necessary and long-lasting structural guarantee for the transcatheter artificial biological valve to meet the symmetry of the valve leaflets and the synchronization of opening and closing; $\hat{2}$ the anchoring stent and the transcatheter valve-in-ring are implanted anterior and posterior respectively, and tightly combined again in the annuloplasty ring to ensure zero displacement of the valve, and meanwhile, the integrated transcatheter valve-in-ring structure is difficult to grip and deliver due to its complex structure; $\hat{3}$ the anchoring stent is designed according to the real anatomical form and the structure of the three-dimensional reconstruction of the pre-operative image data, so that the positioning release can be automatically and adaptively combined and clamped with the supravalvular and subvalvular tissue, and the preset structure with a circular shape is remodeled, so that the transcatheter valve is anchored more precisely; $\hat{4}$ the split type design is expected to improve and solve the many complications caused by the different types, shapes, and structures of the previously implanted annuloplasty ring, and subsequent interventional treatment, in order to achieve better therapeutic effects; $\hat{5}$ in the split type precisely-anchorable transcatheter valve-in-ring system described above, each completion of the transcatheter valve-in-ring treatment process accurately anchored for the personalized preset realization, the analysis of related data, the shape design of the transcatheter valve-in-ring anchoring stent, processing and manufacturing, related data obtained in the whole process of interventional treatment and postoperative follow-up visit data and the like, as an independent data unit, a large amount of personalized image data, an anchoring stent design and related data such as processing and manufacturing parameters, a interventional treatment process and a postoperative result are accumulated, and the intelligent, commercialization and large-scale application of the interve interventional treatment implementation of the split type precisely-anchorable transcatheter valve-in-ring system is gradually realized.

The invention claimed is:

1. A split type precisely-anchorable transcatheter valve-in-ring system, characterized in that, the system comprises a split transcatheter valve-in-ring anchoring stent and a transcatheter artificial biological valve-in-ring, wherein a shape and structure of the transcatheter valve-in-ring anchoring stent are matched with a real structure of a natural annuloplasty ring of a patient, and supravalvular and subvalvular tissues after three-dimensional reconstruction based on imaging data of a failed valve after implantation of an artificial annuloplasty ring;

the transcatheter valve-in-ring anchoring stent has a compressed state in which is it disposed in a catheter, a first anchoring state in which it is released via the catheter, and a second anchoring state in which it is combined with the transcatheter artificial biological valve-in-ring, in the first anchoring state, the transcatheter valve-in-ring anchoring stent is processed and shaped into a conical funnel shape with a large atrial surface and a small ventricular surface according to type, shape and size of the artificial annuloplasty ring previously implanted and the imaging data by three-dimensional reconstruction, the transcatheter valve-in-ring anchoring stent is input via the catheter and released, its deformation and reshaping allow it to adapt to a personalized alignment, bonding and docking with the supravalvular and subvalvular tissues of the failed valve so as to reshape a circular structure;

in the second anchoring state, in the transcatheter valve-in-ring anchoring stent of the first anchoring state, the transcatheter artificial biological valve-in-ring is delivered via the catheter and is released by balloon expansion, and is combined with the transcatheter valve-in-ring anchoring stent, so that the transcatheter valve-in-ring anchoring stent is expanded together with the transcatheter artificial biological valve-in-ring from an original conical funnel shape to a cylindrical shape, and a centripetal return clip generated by a secondary deformation is tightly combined with the transcatheter artificial biological valve-in-ring to complete anchoring with a mitral valve site or a tricuspid valve site and subvalvular tissues;

the transcatheter valve-in-ring anchoring stent is an umbrella tubular stent structure, comprising an atrial surface, a ventricular surface, and an anchoring stent connecting part therebetween, wherein the atrial surface is an umbrella shape corresponding to a real atrial surface's shape which is formed by the three-dimensional reconstruction of the imaging data, that is a first lattice portion; the ventricular surface is a plurality of positioning hook loops precisely aligned with leaflets' junction positions; the anchoring stent connecting part is a funnel shape with a round opening and has a second lattice portion, the anchoring stent connecting part is configured to undergo deformation and expansion to transform from the funnel shape in the first anchoring state to the cylindrical shape in the second anchoring state.

2. The split type precisely-anchorable transcatheter valve-in-ring system according to claim 1, characterized by further comprising a delivery assembly, wherein the delivery assembly comprises a transcatheter valve-in-ring anchoring stent delivery kit and a transcatheter artificial biological valve-in-ring delivery kit.

3. The split type precisely-anchorable transcatheter valve-in-ring system according to claim 1, characterized in that, the artificial-annuloplasty ring previously implanted refers to various types of mitral annuloplasty rings implanted for various etiologies of mitral valve insufficiency, or various types of tricuspid annuloplasty rings implanted for various etiologies of tricuspid valve insufficiency; the shape and structure of the transcatheter valve-in-ring anchoring stent is accurately matched with the type of the artificial annuloplasty ring previously implanted and the imaging data of postoperative valve failure through three-dimensional reconstruction of a real shape and anatomical structure; the transcatheter valve-in-ring anchoring stent and the transcatheter artificial biological valve-in-ring are sequentially inserted, and then reassembled, the transcatheter valve-in-ring anchoring stent deforms again, that is the secondary deformation, due to the release of the transcatheter artificial biological valve-in-ring, and completes anchoring of a diseased mitral valve or tricuspid valve and subvalvular tissue in a circular shape, so that the transcatheter artificial biological valve-in-ring is protected from a stress of the shape of the artificial annuloplasty ring previously implanted, and a persistent stability of a circular anchoring is obtained.

4. The split type precisely-anchorable transcatheter valve-in-ring system according to claim 1, characterized in that, the transcatheter artificial biological valve-in-ring is a mitral valve-in-ring or a tricuspid valve-in-ring.

5. The split type precisely-anchorable transcatheter valve-in-ring system according to claim 1, characterized in that, in the second anchoring state, the transcatheter artificial biological valve-in-ring is delivered by the catheter to the transcatheter valve-in-ring anchoring stent which is in the first state for balloon expansion and release, the balloon expansion's external force causes the transcatheter valve-in-ring anchoring stent to deform again, that is the secondary deformation, and it is combined with the expanded transcatheter artificial biological valve-in-ring, to realize anchoring of the transcatheter valve-in-ring anchoring stent with valve leaflets and subvalvular tissues of a mitral or tricuspid valve site in a circular shape.

6. The split type precisely-anchorable transcatheter valve-in-ring system according to claim 1, characterized in that, the first anchoring state of the anchoring stent connecting part is a shape-setting memory state in vitro of the stent after being delivered and released through the catheter, the shape-setting memory state of the anchoring stent connecting part from the atrial surface to the ventricular surface has a contraction taper, with a taper of 5-45 degrees.

7. The split type precisely-anchorable transcatheter valve-in-ring system according to claim 1, characterized in that, there are two positioning hook loops precisely aligned and matched between two leaflets of a mitral annuloplasty ring, or there are three positioning hook loops precisely aligned and matched with junction positions of three leaflets of a tricuspid annuloplasty ring.

8. The split type precisely-anchorable transcatheter valve-in-ring system according to claim 1, characterized in that, in the first anchoring state of the transcatheter valve-in-ring anchoring stent, the positioning hook loops are released via the catheter in advance of the atrial surface of the transcatheter valve-in-ring anchoring stent, and are inserted into valve leaflets' junction positions of the mitral valve or tricuspid valve matched with the positioning hook loops, so that the atrial surface of the transcatheter valve-in-ring anchoring stent is matched with a real atrial shape; in the second anchoring state after the deformation of the transcatheter valve-in-ring anchoring stent, the positioning hook loops and periphery of the anchoring stent connecting part are filled between a coupling portion of the annuloplasty ring and the transcatheter artificial biological valve-in-ring.

9. The split type precisely-anchorable transcatheter valve-in-ring system according to claim 8, characterized in that, in the second anchoring state, the positioning hook loops are filled in an eccentric region of the artificial annuloplasty ring previously implanted, so that a central axis of the anchoring stent connecting part is coaxial with a center of the artificial annuloplasty ring previously implanted.

10. The split type precisely-anchorable transcatheter valve-in-ring system according to claim 1, characterized in that, positioning hook loops extend from the anchoring stent connecting part to the ventricular surface and then are folded, so as to be matched with a shape of real subvalvular tissues of the failed valve, which is formed by three-dimensional reconstruction of subvalvular imaging data.

11. The split type precisely-anchorable transcatheter valve-in-ring system according to claim 10, characterized in that, in the first anchoring state of the transcatheter valve-in-ring anchoring stent, after the positioning hook loops are released via the catheter, the positioning hook loops are aligned with subvalvular tissues of the failed valve; and in the second anchoring state of the transcatheter valve-in-ring anchoring stent, the plurality of positioning hook loops form a clamping portion through deformation and combined force of the atrial surface and the anchoring stent connecting part of the transcatheter valve-in-ring anchoring stent, and a plurality of deformed positioning hook loops are tightly combined with the leaflets and subvalvular tissues under the failed valve.

12. The split type precisely-anchorable transcatheter valve-in-ring system according to claim 11, characterized in that, the number of the positioning hook loops is 2-9.

13. The split type precisely-anchorable transcatheter valve-in-ring system according to claim 1, characterized in that, the atrial surface's end portion of the anchoring stent connecting part is provided with a plurality of fixed support rods or bending parts for embedding the transcatheter valve-in-ring anchoring stent, the fixed support rods or bending parts are extended in an axial direction of the atrial surface, and the ends thereof are bent towards an axis of the transcatheter valve-in-ring anchoring stent.

14. The split type precisely-anchorable transcatheter valve-in-ring system according to claim 13, characterized in that, the anchoring stent connecting part is provided with centripetally bending parts for embedding a plurality of end heads at an outflow end of the transcatheter valve-in-ring anchoring stent, and the centripetally bending parts and the plurality of fixed support rods or bending parts centripetally surround an upper part and a lower part of the transcatheter valve-in-ring anchoring stent, so as to prevent the transcatheter artificial biological valve-in-ring from moving during the releasing.

15. The split type precisely-anchorable transcatheter valve-in-ring system according to claim 14, characterized in that, the number of the fixed support rods or bending parts is 3-12.

16. The split type precisely-anchorable transcatheter valve-in-ring system according to claim 1, characterized in that, the first lattice portion and the second lattice portion of the transcatheter valve-in-ring anchoring stent are formed by a unit lattice composed of a compressible rhombic lattice, a V-shaped lattice and/or a hexagonal or polygonal lattice, and the first lattice portion is adaptively connected to the second lattice portion.

17. The split type precisely-anchorable transcatheter valve-in-ring system according to claim 1, characterized in that, an outer periphery of the first lattice portion is spaced 1-2 mm from an atrial wall.

18. The split type precisely-anchorable transcatheter valve-in-ring system according to claim 1, characterized in that, an inner peripheral edge diameter of the second lattice portion matches an outer diameter of various corresponding size specifications of the transcatheter artificial biological valve-in-ring.

19. The split type precisely-anchorable transcatheter valve-in-ring system according to claim 1, characterized in that, a layer of medical polymer film is coated on a surface of the transcatheter valve-in-ring anchoring stent.

20. The split type precisely-anchorable transcatheter valve-in-ring system according to claim 1, characterized in that, the atrial surface, the ventricular surface and the anchoring stent connecting parts of the transcatheter valve-in-ring anchoring stent are three-dimensional forming structures or split connecting structures after laser integrated cutting.

21. The split type precisely-anchorable transcatheter valve-in-ring system according to claim 1, characterized in that, the transcatheter valve-in-ring anchoring stent is a metallic material or a non-metallic material having shape-setting memory properties.

22. The split type precisely-anchorable transcatheter valve-in-ring system according to claim 1, characterized in that, the transcatheter artificial biological valve-in-ring comprises a cobalt-chromium alloy stent which is radially compressible and can be expanded by a balloon and is in a cylindrical shape, or a nickel-titanium alloy stent which is radially compressible and self-expandable and has a cylindrical shape, and three fan-shaped leaflets arranged on an inner side of the transcatheter valve-in-ring anchoring stent, wherein the three fan-shaped leaflets each has a free edge, an arc-shaped bottom edge and leaflet junction parts which extend on two sides, and the transcatheter valve-in-ring anchoring stent is a metal net tube.

23. The split type precisely-anchorable transcatheter valve-in-ring system according to claim 17, characterized in that, the stent of the transcatheter artificial biological valve-in-ring is a cobalt-based alloy cobalt or chromium alloy or a nickel-titanium alloy.

24. The split type precisely-anchorable transcatheter valve-in-ring system according to claim 2, characterized in that, regarding the transcatheter valve-in-ring anchoring stent delivery kit and the transcatheter artificial biological valve-in-ring delivery kit, for a tricuspid valve-in-ring, they can be approached from the inferior vena cava via the femoral vein, or from the superior vena cava via the jugular vein or subclavian vein to the tricuspid valve site; and for a mitral valve-in-ring, they can be approached through the apex of the heart, left atrium, or femoral vein via the interventricular septum to the mitral valve site.

* * * * *